(12) United States Patent
Hong et al.

(10) Patent No.: US 11,013,699 B2
(45) Date of Patent: *May 25, 2021

(54) BAKUCHIOL COMPOSITIONS FOR TREATMENT OF POST INFLAMMATORY HYPERPIGMENTATION

(71) Applicant: Unigen, Inc., Tacoma, WA (US)

(72) Inventors: Mei Feng Hong, Seattle, WA (US); Qi Jia, Olympia, WA (US); Lidia Alfaro Brownell, Tacoma, WA (US)

(73) Assignee: Unigen, Inc., Tacoma, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/594,759

(22) Filed: Oct. 7, 2019

(65) Prior Publication Data

US 2020/0030256 A1    Jan. 30, 2020

Related U.S. Application Data

(63) Continuation of application No. 15/628,449, filed on Jun. 20, 2017, now Pat. No. 10,434,073, which is a continuation of application No. 13/365,172, filed on Feb. 2, 2012, now Pat. No. 9,713,596, which is a continuation-in-part of application No. PCT/US2011/026594, filed on Mar. 1, 2011.

(60) Provisional application No. 61/438,890, filed on Feb. 2, 2011.

(51) Int. Cl.
| | | |
|---|---|---|
| *A61K 31/05* | (2006.01) | |
| *A61K 31/60* | (2006.01) | |
| *A61K 8/34* | (2006.01) | |
| *A61Q 19/02* | (2006.01) | |

(52) U.S. Cl.
CPC .............. *A61K 31/05* (2013.01); *A61K 8/347* (2013.01); *A61K 31/60* (2013.01); *A61Q 19/02* (2013.01); *A61K 2800/30* (2013.01)

(58) Field of Classification Search
None
See application file for complete search history.

(56) References Cited

U.S. PATENT DOCUMENTS

| | | | | |
|---|---|---|---|---|
| 9,713,596 | B2 * | 7/2017 | Hong | A61K 31/05 |
| 10,434,073 | B2 * | 10/2019 | Hong | A61P 17/00 |
| 2006/0251749 | A1 * | 11/2006 | Jia | A61K 36/487 |
| | | | | 424/757 |
| 2010/0189669 | A1 * | 7/2010 | Hakozaki | A61K 8/9789 |
| | | | | 514/1.1 |

* cited by examiner

*Primary Examiner* — Michael P Cohen
(74) *Attorney, Agent, or Firm* — Sandra Thompson; Finlayson Toffer Roosevelt & Lilly LLP

(57) ABSTRACT

Methods for treating excess pigmentation, including treatment of post inflammatory hyperpigmentation (PIH), are disclosed. The disclosed methods comprise administration of a composition comprising bakuchiol substantially free of furanocoumarins to a mammal. Compositions comprising bakuchiol and methods for their preparation are also disclosed.

19 Claims, 7 Drawing Sheets

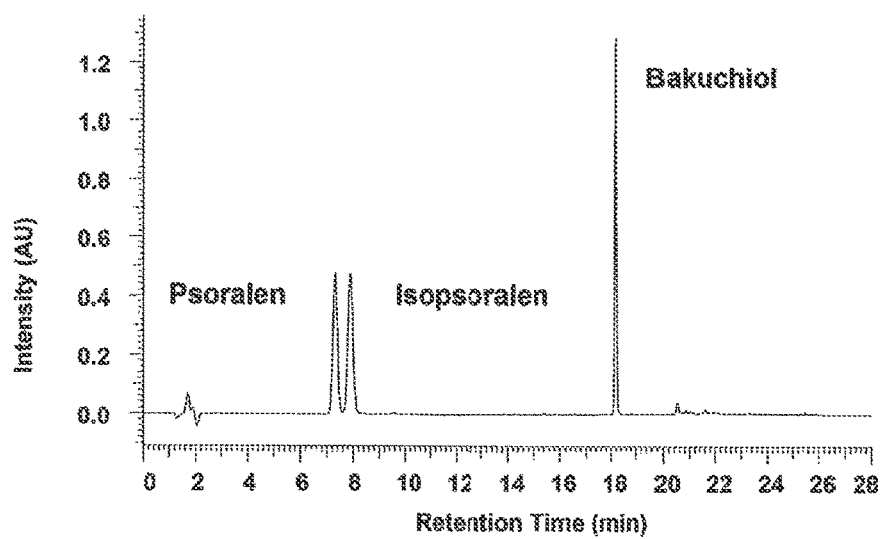
Figure 1. HPLC Chromatogram of Bakuchiol, Psoralen and Isopsoralen Standards

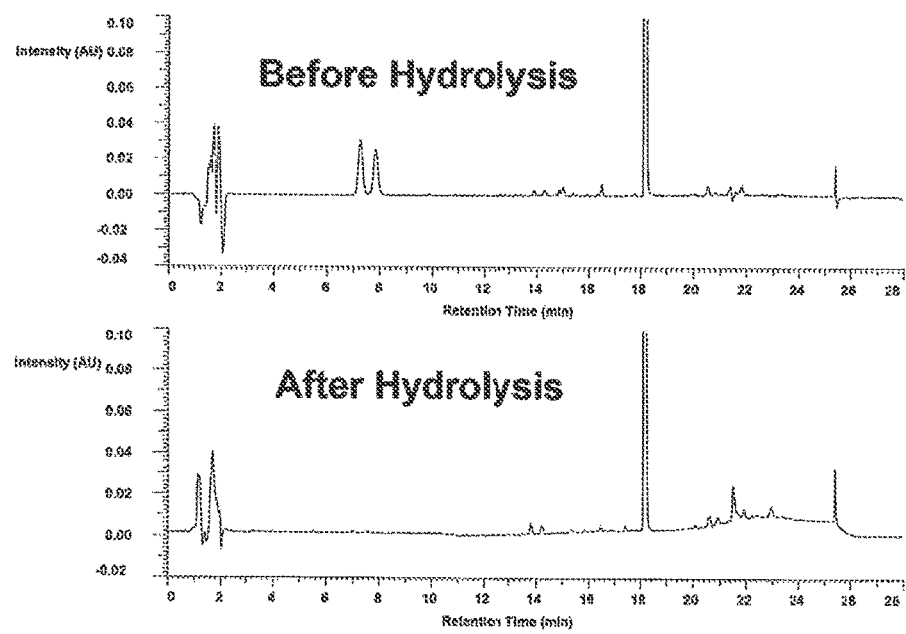
Figure 2. HPLC Chromatogram of Bakuchiol Compositions Before and After Base Hydrolysis Figure 3. Protection from ROS. Cells were plated and treated with test compounds alone and with 4-TBP at two concentrations to assess the protective properties of the test compounds against 4-TBP induced ROS. As a positive control, TBHP, an activated form of $H_2O_2$ as well as 4-TBP treatment in a dose dependent manner was used. Treatment induced fluorescence indicating ROS presence. UP256 ameliorated the effects of the treatment with 4-TBP while sustaining viability.

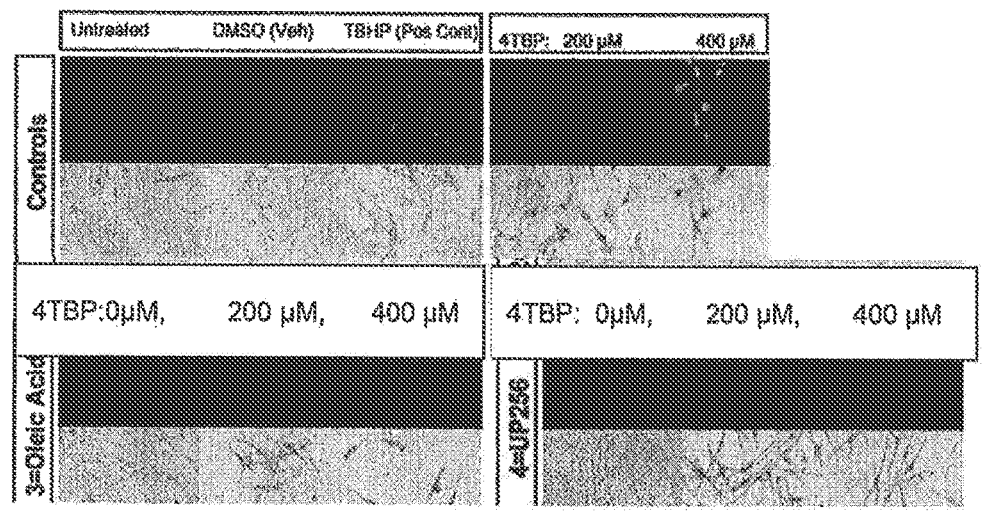

Figure 4. Tyrosinase Inhibition Assay of Two Bakuchiol Compositions
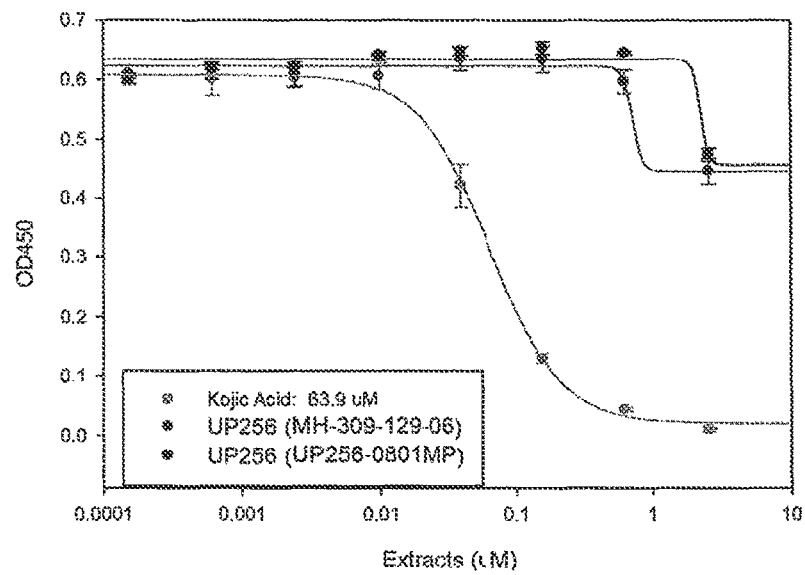
Figure. 5 Changes in PIH Severity of Individual Subjects
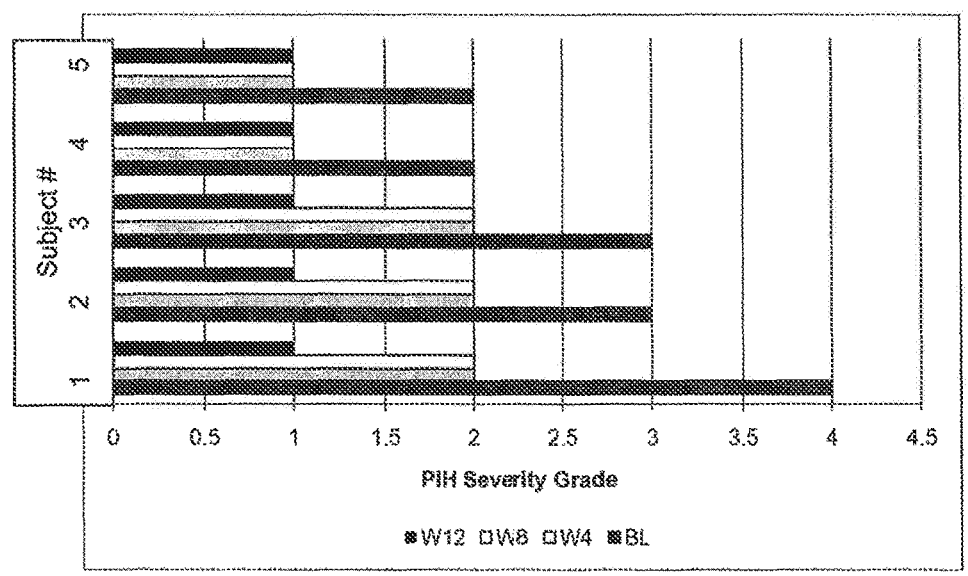

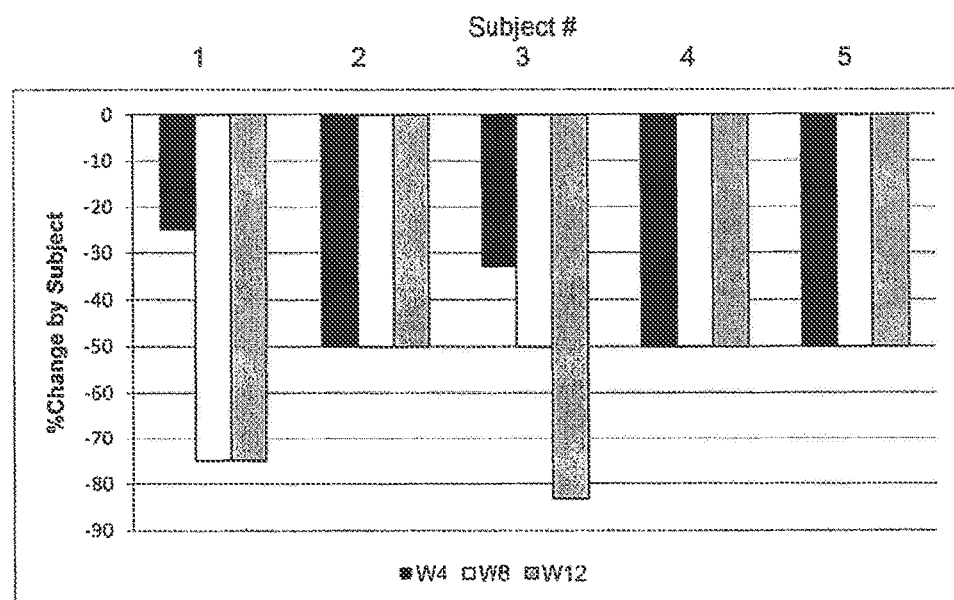
Figure. 6 Percent Changes on PIH Affected Facial Area of Individual Subjects.

Figure 7. Mean Percentage Changes in PIH & PIH Severity of Five Subjects.
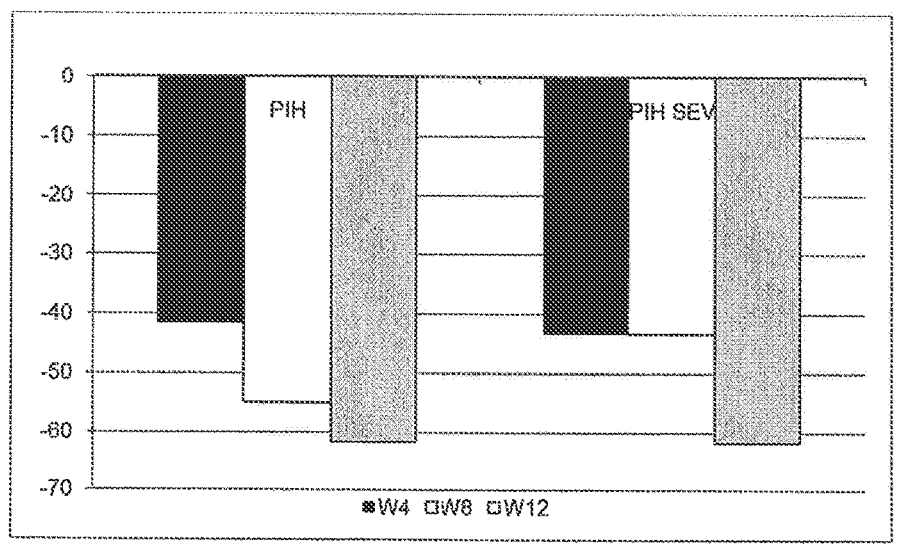
Figure 8. Mean Grade Level Reductions of PIH and PIH Severity at Each Visit from Baseline.
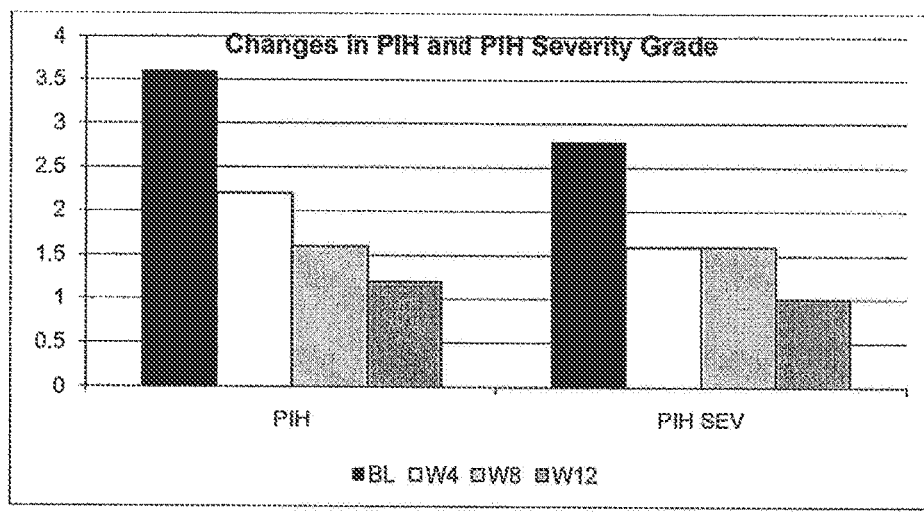

Figure 9. Photos of two study participants
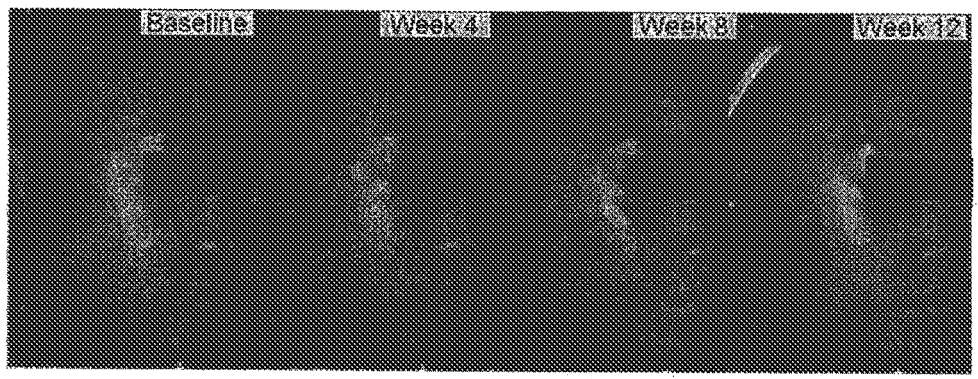
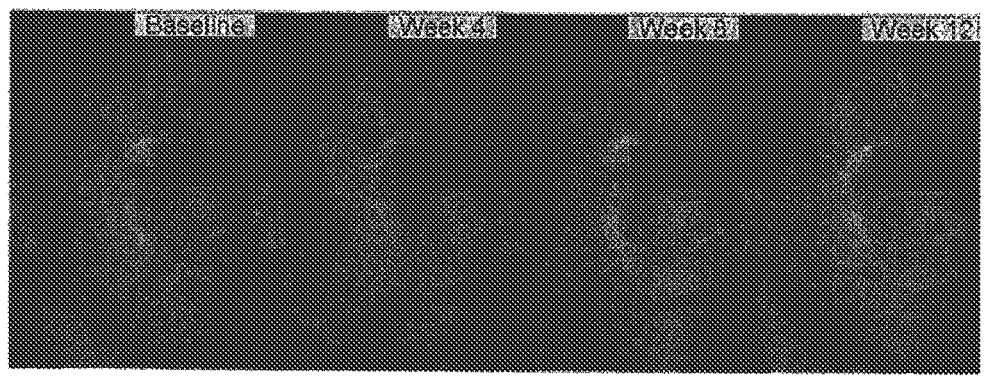

BAKUCHIOL COMPOSITIONS FOR TREATMENT OF POST INFLAMMATORY HYPERPIGMENTATION

CROSS-REFERENCE TO RELATED APPLICATION

This application is a continuation application of U.S. Ser. No. 15/628,449 entitled "Bakuchiol Compositions for Treatment of Post Inflammatory Hyperpigmentation" and filed on Jun. 20, 2017, which is a continuation of U.S. Pat. No. 9,713,596 entitled "Bakuchiol Compositions for Treatment of Post Inflammatory Hyperpigmentation" and filed on Feb. 2, 2012, which is a continuation in part of Patent Cooperation Treaty Serial No.: PCT/US2011/026594 entitled "Bakuchiol Compositions for Treatment of Post Inflammatory Hyperpigmentation", which was filed on Mar. 1, 2011, which claims priority to U.S. Provisional Application Ser. No. 61/438,890 entitled "Bakuchiol Compositions for Treatment of Post Inflammatory Hyperpigmentation" and filed on Feb. 2, 2011.

BACKGROUND

Technical Field

The present invention generally relates to bakuchiol compositions and their rise for treatment of post inflammatory hyperpigmemation.

Description of the Related Art

Post inflammatory hyperpigmentation (PIH) is a unique skin pigmentation condition that involves increased melanin synthesis and deposition, PIH is also characterized by apoptosis of melanocyte cells due to oxidative stress and assaults from mediators and cytokines of inflammatory and immune responses. The melanin deposition (i.e., hyperpigmentation) occurs beyond the epidermal level, with significant melanin being released into the papillary dermis and trapped by large immune cells. These unique histological characteristics of NH present a number of difficulties for treatment of PIH with traditional agents.

Common treatments for PIH are focused on prevention of further pigment development by controlling inflammation with corticosteroids and using photoprotection agents. Chemical peeling compounds, such as salicylic acid and glycolic acid, are also used to facilitate the skin renewal function and to remove or diminish the pigmentation. Topical retinoids have also been used to treat PIH, but such methods require up to 40 weeks before significant benefits are seen.

Tyrosinase inhibitors, or skin whiteners, such as hydroquinone, azelaic acid, kojic acid and licorice extract, have also been employed for treatment of PIH. One significant disadvantage of using traditional skin whitening agents or tyrosinase inhibitors is the non-specific discolorization of the regular skin near the PIH site. This effect reduces the color of the background skin and makes the PIH sites more prominent. Thus, these agents must be applied very carefully over the site of the PIH. In addition, tyrosinase inhibitors are only effective for epidermal hyperpigmentation since this is the location of melanin synthesis by tyrosinase. Because post inflammatory pigmentation is in a deep layer of the skin (e.g., papillary dermis), it takes more than 6 months of continued application of hydroquinone medication before visual changes of the dark marks are seen. Finally, hydroquinone type skin whiteners or tyrosinase inhibitors are associated with side effects including skin irritation, dryness, teratogenicity and induction of vitilago and skin cancers.

Post inflammatory hyperpigmentation can be derived from endogenous inflammatory skin disorders such as acne, atopic dermatitis, allergic contact dermatitis, incontinent pigmenti, lichen planus, lupus erythematosus, morphea. Other causes of PIH include exogenous inflammatory stimuli such as mechanical trauma, ionizing and nonionizing radiation, burns, laser therapies and skin infections. Current therapeutic agents for the above skin disorders are ineffective for preventing, alleviating, reducing or treating PIH. For example, the above skin disorders are often treated with anti-inflammatory agents, such as retinoids, COX inhibitors (e.g., salicylic acid), nonsteroidal anti-inflammatory drugs (NSAIDs), antimicrobial agents or hormonal drugs, hut these treatments have been shown to be ineffective against PHI While significant advances have been made in the field, there continues to be a need in the art for methods for preventing, alleviating, reducing or treating excess pigmentation. For example, methods for treatment of post inflammatory hyperpigmentation are needed. The present invention fulfills these needs and provides farther related advantages.

BRIEF SUMMARY in general terms, the current invention is directed to methods for preventing, alleviating, reducing or treating excess pigmentation. The excess pigmentation may be a result of a condition derived from an inflammatory skin condition. For example, one embodiment of the present invention is a method for preventing, alleviating, reducing or treating post inflammatory hyperpigmentation (PIH). Such PIM may be derived from any number of skin disorders, including acne. The method comprises administering an effective amount of a composition comprising bakuchiol and less than 500 ppm total furanocoumarin impurities to a mammal.

In contrast to other skin lightening agents, the presently disclosed bakuchiol compositions are not tyrosinase inhibitors. Thus, the disclosed compositions specifically decolorize at the PIH site and are useful for treating hyperpigmentation in the deep layers of skin (e.g., papillary dermis). Accordingly, the presently disclosed methods comprise certain advantages over previous methods for treatment of hyperpigmentation and/or PIH.

Accordingly, one embodiment of the present disclosure is directed to a method for preventing, alleviating, reducing or treating excess pigmentation resulting from a condition derived from an inflammatory skin disorder, the method comprising, administering to a mammal an effective amount of a composition comprising bakuchiol, or a pharmaceutically acceptable salt thereof, and a pharmaceutically acceptable carrier and less than 500 ppm total furanocoumarin impurities.

In some embodiments, the condition is post inflammatory hyperpigmentation. In other embodiments, the composition comprises less than 100 ppm total furanocoumarin impurities. In other embodiments, the furanocoumarin impurities comprise psoralen, isopsoralen or combinations thereof. In certain embodiments, the composition shows no tyrosinase inhibition activity relative to a kojic acid control.

In yet other embodiments, the bakuchiol is chemically synthesized or isolated from a plant. For example, in some embodiments the bakuchiol is isolated from a plant. In some further embodiments, the plant is from the *Psoralea* genus of plants, for example, *Psoralea corylifolia* L. (Luguminosae) or *Psoralea glanduloso* L. (Papilionaceae).

In other embodiments, the bakuchiol is isolated from seeds, stems, bark, twigs, tubers, roots, root bark, young shoots, rhixomes, flowers or other reproductive organs, leaves or other aerial parts, or combinations thereof.

In some other embodiments, the post inflammatory hyperpigmentation (PIH) is derived from acne, atopic dermatitis, allergic contact dermatitis, incontinent pigmenti, lichen planus, lupus erythematosus, morphea, mechanical trauma, ionizing or nonionizing, radiation, burns, laser or drug therapies, skin infection or combinations thereof. For examples, in certain aspects the post inflammatory hyperpigmentation (PIH) is derived from acne.

In other embodiments, the composition comprises 0.001% to 99.9% by total weight of bakuchiol and a pharmaceutically, dermatologically or cosmetically acceptable carrier. For example, in some aspects the composition comprises from 0.1% to 2.0% by total weight of bakuchiol, 1.0% by total weight of bakuchiol or 0.5% by total weight of bakuchiol.

In other embodiments, the dermatologically acceptable carrier comprises a nonsticking gauze, a bandage, a swab, a cloth wipe, a patch, a mask or a protectant. In some other embodiments, the cosmetically acceptable carrier comprises a cleanser or an antiseptic.

In some aspects, the composition is formulated for topical administration. For example, in some aspects the composition further comprises a cream, a lotion, an ointment, a gel, an emulsion, a liquid, a paste, a soap, a powder or combinations thereof.

In other embodiments the composition further comprises an adjuvant, skin penetration enhancer or liposomes. In yet other embodiments, the adjuvant comprises α-hydroxyacids salicylic acid, linoleic acid, retinoids, benzoyl peroxide, sodium sulfacetamide, clindamycin, erythromycin, dapsone, tetracycline, doxycyclin, minocyclin, zinc, estrogen or derivatives thereof, anti-androgens, sulfur, corticosteroids, cortisone, tazarotene, curcumin extract, acacia extract, scutellaria extract, green tea extract, grape seed extract or combinations thereof.

In certain embodiments, the composition is formulated in a capsule, for example, controlled release capsule. In other embodiments, the composition is administered topically, by aerosol, by suppository, intradermically intramuscularly or intravenously.

In some aspects, the method prevents excess pigmentation. In other aspects, the method alleviates excess pigmentation. In yet other aspects, the method reduces excess pigmentation. In still other aspects, the method treats excess pigmentation.

In other embodiments, the excess pigmentation occurs in a deep layer of skin, for example in a papillary dermis layer of skin. In other embodiments, the method further comprises reducing super oxide anion. In some other embodiments, the method further comprises reducing melanogenesis. In yet other embodiments, the method further comprises reducing melanocyte proliferation. In still other embodiments, the method further comprises preventing melanocyte apotosis.

In certain other embodiments, the mammal is a human. In some other embodiments, the mammal is in need of preventing, alleviating, reducing or treating excess pigmentation resulting from a condition derived from an inflammatory skin disorder. For example, the mammal may be in need of treatment for PIH.

In another embodiment, the present disclosure is directed to a method for reducing melanogenesis, reducing melanocyte proliferation or preventing melanocyte apotosis, the method comprising administering to a mammal an effective amount of a composition comprising bakuchiol, or a pharmaceutically acceptable salt thereof, and a pharmaceutically acceptable carrier and less than 500 ppm total furanocoumarin impurities. In some further embodiments, the method further comprises reducing super oxide anion.

In other embodiments, the composition comprises less than 100 ppm total furanocoumarin impurities. In other embodiments, the furanocoumarin impurities comprise psoralen, isopsoralen or combinations thereof. In certain embodiments, the composition shows no tyrosinase inhibition activity relative to a kojic acid control.

In yet other embodiments, the bakuchiol is chemically synthesized or isolated from a plant. For example, in some embodiments the bakuchiol is isolated from a plant. In some further embodiments, the plant is from the *Psoralea* genus of plants, for example, *Psoralea corylifolia* L. (Luguminosae) or *Psoralea glandulosa* L. (Papilionaceae).

In other embodiments, the bakuchiol is isolated from seeds, stems, bark, twigs, tubers, roots, root bark, young shoots, rhixomes, flowers or other reproductive organs, leaves or other aerial parts, or combinations thereof.

In some embodiments, the melanogenesis, the melanocyte proliferation or the melanocyte apotosis is a result of post inflammatory hyperpigmentation (PIH). In some other embodiments, the post inflammatory hyperpigmentation (PIH) is derived from acne, atopic dermatitis, allergic contact dermatitis, incontinent pigmenti, lichen planus, lupus erythematosus, morphea, mechanical trauma, ionizing or nonionizing radiation, burns, laser or drug therapies, skin infection or combinations thereof. For examples, in certain aspects the post inflammatory hyperpigmentation (PIH) is derived from acne.

In other embodiments, the composition comprises 0.001% to 99.9% by total weight of bakuchiol and a pharmaceutically, dermatologically or cosmetically acceptable carrier. For example, in some aspects the composition comprises from 0.1% to 2.0% by total weight of bakuchiol, 1.0% by total weight of bakuchiol or 0.5% by total weight of bakuchiol.

In other embodiments, the dermatologically acceptable carrier comprises a nonsticking gauze, a bandage, a swab, a cloth wipe, a patch, a mask or a protectant. In some other embodiments, the cosmetically acceptable carrier comprises a cleanser or an antiseptic.

In some aspects, the composition is formulated for topical administration. For example, in some aspects the composition further comprises a cream, a lotion, an ointment, a gel, an emulsion, a liquid, a paste, a soap, a powder or combinations thereof.

In other embodiments the composition further comprises an adjuvant, skin penetration enhancer or liposomes. In yet other embodiments, the adjuvant comprises α-hydroxyacids, salicylic acid, linoleic acid, retinoids, benzoyl peroxide, sodium sulfacetamide, clindamycin, erythromycin, dapsone, tetracycline, doxycyclin, minocyclin, zinc, estrogen or derivatives thereof, anti-androgens, sulfur, corticosteroids, cortisone, tazarotene, curcumin extract, acacia extract, scutellaria extract, green tea extract, grape seed extract or combinations thereof.

In certain embodiments, the composition is formulated in a capsule, for example, controlled release capsule. In other embodiments, the composition is administered topically, by aerosol, by suppository, intradermically, intramuscularly or intravenously.

In some aspects, the method prevents excess pigmentation. In other aspects, the method alleviates excess pigmentation. In yet other aspects, the method reduces excess pigmentation. In still other aspects, the method treats excess pigmentation. In some embodiments, the excess pigmentation occurs in a deep layer of skin, for example, in a papillary dermis layer of skin.

In some other embodiments, the method reduces melanogenesis. In yet other embodiments, the method reduces melanocyte proliferation. In still other embodiments, the method prevents melanocyte apoptosis.

In certain other embodiments, the mammal is a human. In some other embodiments, the mammal is in need of treatment to reduce melanogenesis, reduce melanocyte proliferation or prevent melanocyte apoptosis.

In still other embodiments, the composition further comprises salicylic acid or a pharmaceutically acceptable salt thereof.

Other embodiments of the present disclosure are directed to a method of treating inflammatory or non-inflammatory lesions, the method comprising administering an effective amount of a composition comprising bakuchiol or pharmaceutically acceptable salt thereof and salicylic acid or a pharmaceutically acceptable salt thereof and a pharmaceutically acceptable carrier to a mammal. For example, in some embodiments the lesions comprise inflammatory acne lesions. In other embodiments, the method treats inflammatory and non-inflammatory lesions.

In certain other embodiments of the foregoing, the mammal is a human. In some other embodiments, the mammal is in need of treatment of inflammatory or non-inflammatory lesions.

In other embodiments, the present invention includes a composition comprising bakuchiol or pharmaceutically acceptable salt thereof and salicylic acid or a pharmaceutically acceptable salt and a pharmaceutically acceptable carrier. In certain embodiments, the composition is formulated for topical administration.

These and other aspects of the invention will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

FIG. 1 depicts a chromatogram of bakuchiol, psoralen and isopsoralen standards.

FIG. 2 shows chromatograms of bakuchiol compositions before and after hydrolysis.

FIG. 3 presents data showing the strong antioxidant properties of bakuchiol compositions.

FIG. 4 is a graph of tyrosinase inhibition activity of bakuchiol compositions and kojic acid.

FIG. 5 shows changes in PIH severity of individual test subjects.

FIG. 6 presents a graph of the percent change of PIH affected facial area of individual test subjects.

FIG. 7 demonstrates mean percentage change in PIH and PIH severity of five test subjects.

FIG. 8 depicts the mean grade level reduction of PIH and PIH severity at each visit compared to baseline.

FIG. 9 shows photos of two study participants at various time intervals.

DETAILED DESCRIPTION

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Definitions

As used herein, and unless the context dictates otherwise, the following terms have the meanings as specified below.

"Bakuchiol" as used herein refers to the compound having the following formula:

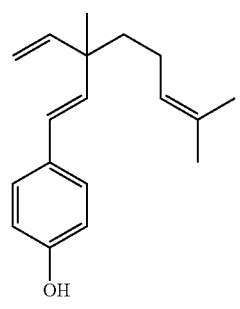

Bakuchiol wherein the benzylic double-bond may be either cis or trans. As used herein, bakuchiol includes pharmaceutically acceptable salts and tautomers of bakuchiol. Phenolic compounds structurally related to bakuchiol are also included within this definition.

"Bakutrol™" is a composition comprising bakuchiol and may also further comprise fatty acids extracted from *Psoralea* plants.

"UP256" refers to a 0.5% (wt/wt) formulation of bakuchiol.

"Preventing", "prevention" and "prevent" in the context of the disclosed methods all refer to prophylactic methods which hinder or stop the occurrence of a particular condition, for example PIH.

"Alleviating", "alleviation" and "alleviate" in the context of the disclosed methods all refer to lessening or mitigating the effects or symptoms of a particular condition, for example PIH.

"Reducing", "reduction" and "reduce" in the context of the disclosed methods all refer to decreasing the effects or symptoms of a particular condition, for example PIH.

"Treating", "treatment" and "treat" in the context of the disclosed methods all refer to techniques or methods intended to improve the symptoms of or decrease or stop the occurrence of a particular condition, for example PIH.

"Impurity" includes any substance that is not wanted in the bakuchiol composition, typically resulting from the isolation of bakuchiol from natural sources. The term impurity includes, but is not limited to furanocoumarin compounds including, but not limited to, psoralen, isopsoralen and other coumarin type impurities. Impurities also refer to impurities resulting from synthetic processes to obtain these compositions.

"Therapeutic" includes treatment and/or prophylaxis. When used, therapeutic refers to humans as well as other animals.

"Pharmaceutically, cosmetically or therapeutically effective dose or amount" refers to a dosage level sufficient to induce a desired biological or functional result. That result may be the alleviation of the signs, symptoms or causes of a disease, a skin condition or any other alteration of a biological system that is desired.

"Placebo" refers to the substitution of the pharmaceutically or therapeutically effective dose or amount dose sufficient to induce a desired biological that may alleviate the signs, symptoms or causes of a disease with a non-active substance.

A "host" or "subject" or "patient" is a living subject, human or animal, into which the compositions described herein are administered. Thus, the compositions described herein may be used for veterinary as well as human applications and the terms "patient" or "subject" or "host" should not be construed in a limiting manner. In the case of veterinary applications, the dosage ranges can be determined as described below, taking into account the body weight of the animal.

As noted above, one embodiment of the present disclosure relates to use of a composition comprising bakuchiol essentially free of furanocoumarin impurities for prevention, alleviation, reduction or treatment of excess pigmentation resulting from a condition derived from an inflammatory skin disorder. For example, the disclosed methods are useful for treatment of post inflammatory hyperpigmentation (PIH). In certain embodiments, the PIH may be derived from acne. The disclosed method has demonstrated human clinical efficacy in prevention, alleviation, reduction, and treatment of post inflammatory hyperpigmentation derived from skin disorders such as acne, atopic dermatitis, allergic contact dermatitis, incontinent pigmenti, lichen planus, lupus erythematosus, morphea; and post inflammatory hyperpigmentation caused by mechanical trauma, ionizing and non-ionizing radiation, burns, laser and drug therapies, and skin infections by using a synthetic bakuchiol or furanocoumarin free *psoralea* extract bakuchiol composition. These and other aspects and various embodiments of the present disclosure will become evident upon reference to the description which follows.

A. Bakuchiol Compositions

In one embodiment, the present disclosure provides a composition comprising bakuchiol, which is substantially free of impurities, particularly furanocoumarin impurities. This composition is also referred to herein as Bakutrol™. In some embodiments, the composition is obtained by organic synthesis from simple compounds as demonstrated in the literature (Hongli Chen and Yuanchao Li, Letters in Organic Chemistry, 2008, 5, 467-469) or from a plant. In certain embodiments, the bakuchiol composition is isolated from a plant. Plant sources of bakuchiol include the family of plants including, but not limited to Luguminosae, Papilionaceae, Lauraceae and Magnoliaceae and the genus of plants including, but not limited to *Psorlea, Sassafras, Magnolia* and *Astractylodes*. For example, the bakuchiol compositions may be isolated from *Psoralea corylifolia* L. (Luguminosae) or *Psoralea glandulosa* L. (Papilionaceae). The compositions may be obtained from the whole plant or from one or more individual parts of the plant including, but not limited to the seeds, stems, bark, twigs, tubers, roots, root bark, young shoots, rhixomes, flowers and other reproductive organs, leaves and other aerial parts or combinations thereof. Methods for isolation of bakuchiol from plants may include solvent extraction, supercritical fluid extraction, distillation, physical compressing or combinations thereof.

Bakuchiol, the structure of which is illustrated below, is a phenolic compound having a single hydroxyl group on the aromatic ring and an unsaturated hydrocarbon chain. Although represented as trans in the structure below, the benzylic double bond of bakuchiol may also be cis.

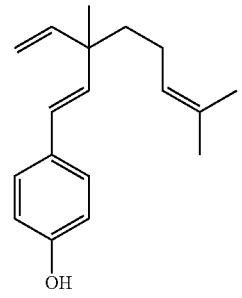

Bakuchiol

The amount of Bakuchiol (i.e., weight percent (w/w %)) in the purified plant extract depends on the method of extraction and the extent of purification of the crude extract. In one embodiment the amount of bakuchiol in the extract is in the range from 13.7% to 29.1% as shown in the Table 2. In other embodiments the amount of bakuchiol in the extract is at least 30%, at least 35%, at least 40%, at least 45%, at least 50%, at least 60%, at least 70%, at least 80% or at least 90%. In certain embodiments, the amount of Bakuchiol in the extract is 100%. In other certain embodiments, the amount of bakuchiol in the composition is not less than 60%. Examples 6-8 provide examples of extracts comprising various amounts of bakuchiol.

Although bakuchiol is a biologically active natural product having a great deal of potential for use in the prevention and treatment of various diseases and conditions, there are a number of limitations associated with the use of this compound. Some limitations include its low concentration in natural sources and the presence of co-existing toxic components in the bakuchiol source. The impurities present in the bakuchiol compositions will vary with the source of the bakuchiol. For example, psoralens, also known as furanocoumarins, are naturally occurring secondary metabolites in *Psoralea* genus plants (a source of bakuchiol) and also exist in many fruits and vegetables. Examples of furanocoumarins often found co-existing with bakuchiol include psoralen and isopsoralen.

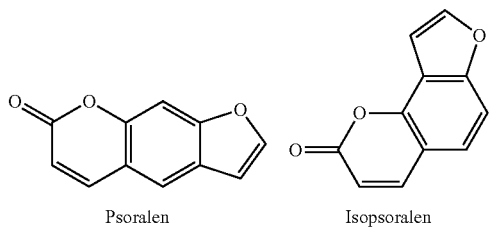

Psoralen                    Isopsoralen

A number of health risks have been associated with the handling, topical application and ingestion of psoralen-containing plants and synthetic psoralens. Psoralens are well known to be phototoxic agents, which increase the sensitivity of skin to ultra violet radiation and promotes skin cancer (Epstein (1999) Med. Surg. 18(4):274-284). Psoralen has been shown to induce growth inhibition in rats (Diawara et al. (1997) Cancer Lett. 114(1-2):159-160). Gonadal toxicity from crude extracts of *Psoralea* plants has been linked directly with the disruption of the hypothalamus-pituitary-gonadal axis (Takizawa et al. (2002) J. Toxicological Sciences 27(2):97-105). Oral administration of the psoralens, bergapten (5-methoxypsoralen) and xanthotoxin (8-methoxypsoralen), in the diet of female rats reduced birthrates, the number of implantation sites, pups, corpora lutea, full and empty uterine weight and circulating estrogen levels in a dose-dependent manner (Diawara et al. (1999) J. Biochem. Molecular Toxicology 13(3/4):195-203). Psoralens have also been shown to induce the mRNAs of the liver enzymes CYPIA1 and UGTIA6, suggesting that enhanced metabolism of estrogens by psoralens may explain the reproductive toxicity and the observed reduction of ovarian follicular function and ovulation (Diawara et al. (May-June 2003) Pediatr Pathol Mol Med. 22(3):247-58.) Because of the toxicity of furanocoumarins, it is important to remove psoralen and isopsoralen from bakuchiol compositions intended for treating post inflammatory hyperpigmentation or other conditions.

Psoralen and isopsoralen account for about 0.1-2% of the dry weight of *Psoralea* seeds and about 1-20% of the weight in solvent or super-critical fluid extracts. Crude extracts from a *Psoralea* genus plant can be obtained by solvent extraction, or super-critical fluid extraction, distillation, physical compressing or a combination of above extraction methods. An enriched Bakuchiol composition can be obtained by chromatographic separations, solvent partitions (India patent publication #00570/KOL/2005), distillations, recrystallizations and other wet chemistry and physical processes. Published US Patent Application No. 2006/0251749, which is hereby incorporated by reference in its entirety, discloses a solvent extraction followed by hydroxylation to break down furanocoumarin rings and obtain an enriched bakuchiol composition essentially free of furanocoumarin impurities (e.g., less than 500 ppm, or less than 100 ppm furanocoumarin impurities). The published method comprises the steps of extraction of the compound from a plant source, hydrolysis of the crude extract with a basic solution under heat, and purification by a method including but not limited to column chromatography, extraction followed by crystallization, solvent partition, recrystallization and combinations thereof. The present Applicants have discovered that such a composition of a bakuchiol enriched *psoralea* extract essentially free of furanocoumarin impurities can be utilized for prevention, alleviation, reduction or treatment of excess pigmentation. For example, the disclosed bakuchiol compositions are effective for prevention, alleviation, reduction, or treatment of post inflammatory hyper pigmentation (PIH).

The present disclosure is also directed to methods for isolating and purifying crude compositions of bakuchiol and related compounds obtained from natural sources. The method for isolating and purifying these compositions comprises the steps of extraction of the compounds from a plant source, hydrolysis of the crude extract with a basic solution, and purification by a method including but not limited to column chromatography, extraction followed by crystallization, solvent partition, recrystallization and combinations thereof. Crude extracts purified in this manner are essentially free of furanocoumarin impurities such as psoralen and isopsoralen. Thus, the potential phototoxicity, topical irritation, carcenogenecity, and reproductive toxicity associated with these compounds are essentially eliminated.

In certain embodiments, the disclosed compositions comprise less than 500 ppm, less than 250 ppm, less than 100 ppm, or less than 50 ppm total furanocoumarin impurities. The concentration of furanocoumarin impurities may be determined by any means known to one skilled in the art. For example, in one embodiment the furanocoumarin content may be determined by HPLC.

The efficiency of bakuchiol extraction from plant sources was evaluated using six different organic solvent systems under two sets of extraction conditions as described in Example 2. The results are set forth in Table 2. With reference to Table 2, it can be seen that bakuchiol can be extracted from *Psoralea* plants with any number of organic solvents and/or combinations thereof. The amount of bakuchiol in the various extracts ranged from 13.7% to 29.1% by weight. Other extraction methods include, but are not limited to, $CO_2$ super-critical fluid extraction and water distillation. Squeeze exudates from fresh plant parts such as seeds, can also be utilized to obtain Bakuchiol compositions from natural sources.

The efficacy of purification of crude bakuchiol extracts by column chromatography is demonstrated in Example 3 and Table 3. Eight different types of resins were evaluated specifically for their ability to separate bakuchiol from furanocoumarin impurities. Both silica gel and CG-161 resins demonstrated satisfactory separation. Column chromatographic separation of crude plant extracts on an industrial scale, however, is typically not economically feasible because it requires expensive equipment and reagents and experienced personnel. The extremely low loading capacity of these samples due to the complexity of crude plant extracts also makes industrial scale column chromatography difficult.

Example 4 describes an economical method for separating bakuchiol from furanocoumarin impurities. The method comprises treatment of compositions containing furanocoumarin impurities with a base. As illustrated by the following Scheme 1, using NaOH for purposes of illustration, heating with a base opens up the lactone ring of the furanocoumarins, thereby converting them into the corresponding salts of carboxylic acids. These salts can then be easily separated from the remainder of the mixture by a variety of methods. The disclosed method allows preparation of bakuchiol compositions essentially free of furanocoumarin impurities (e.g., less than 500 ppm). Such highly pure bakuchiol compositions are not attainable using standard chromatographic techniques without the disclosed hydrolysis.

Reaction Scheme 1. Hydrolysis of Furanocoumarins

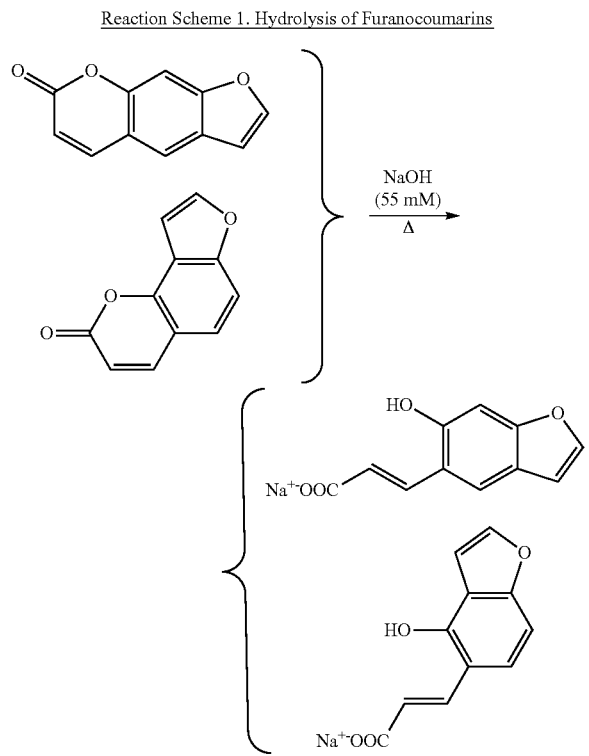

The basic solution may comprise any base capable of opening lactone rings, including, but not limited to sodium hydroxide, potassium hydroxide, calcium hydroxide, lithium hydroxide or combinations thereof. The solution can have different concentration and pH values to maximize the conversion to the acid salt. The reaction mixture can also be heated under different temperature and pressures to maximize the reaction rate, efficiency and yield.

The course of the reaction can be followed by HPLC to ensure complete conversion of the furanocoumarins into their respective carboxylic acid salts. HPLC chromatograms of the crude composition before and after hydrolysis are illustrated in FIG. 2. Upon completion of the reaction (as determined by HPLC), the reaction solution can be processed using various methods, including but are not limited to column chromatography, crystallization, solvent partition, precipitation, solvent wash or combinations thereof. Organic solvents that can be used for solvent partitioning include, but are not limited to petroleum ether, ethyl acetate, ethyl ether, hexane, chloroform, propanol, butanol, and methylene chloride, as well as other water immiscible organic solvents.

Crude extracts purified in this manner are essentially free of furanocoumarin impurities such as psoralen and isopsoralen. For example, the purified extract may comprise less than 500 ppm, less than 250 ppm, less than 100 ppm or even less than 50 ppm furanocoumarin impurities. Additionally, the color of these highly pure furanocoumarin free, bakuchiol compositions is light brown or red and they are very stable with respect to both color and composition of the active agent, making them particularly suitable for formulation, storage and cosmetic applications.

Also included in the present disclosure is a method for analyzing compositions of bakuchiol, which enables detection and quantification of impurities. In this embodiment, the method for analyzing compositions of bakuchiol is comprised of the step of analyzing the compositions by high-pressure liquid chromatography (HPLC). Analysis by HPLC enables quantification of the various components in the mixture and also provides a means to track bakuchiol, psoralen, isopsoralen and other natural components in *Psoralea* plants to guide the extraction, hydrolysis and purification processes. A method for analyzing compositions of bakuchiol using high pressure liquid chromatography (HPLC) is described in Example 1 (Table 1).

B. Treatment of Excess Pigmentation with Bakuchiol Compositions

One embodiment of the present disclosure relates to use of a composition comprising bakuchiol essentially free of furanocoumarin impurities for prevention, alleviation, reduction or treatment of excess pigmentation resulting from a condition derived from an inflammatory skin disorder. For example, the disclosed methods include prevention, alleviation, reduction or treatment of post inflammatory hyperpigmentation (PIH). In certain embodiments, the PIH may be derived from acne. The disclosure includes the formulation of a bakuchiol composition in a typical cosmetic vehicle and also in skin care cream, gel lotion and other formulations as discussed in more detail below. As shown in the Examples, the present Applicants have demonstrated the un-expected human clinical efficacy of bakuchiol compositions in prevention, alleviation, reduction or treatment of post inflammatory hyperpigmentation (PIH) derived from skin disorders such as acne, atopic dermatitis, allergic contact dermatitis, incontinent pigmenti, lichen planus, lupus erythematosus, morphea; and post inflammatory hyperpigmentation caused by mechanical trauma, ionizing and nonionizing radiation, burns, laser and drug therapies, and skin infections.

The disclosed methods comprise administering to a mammal (e.g., a human patient) an effective amount of a composition comprising bakuchiol, which is substantially free of furanocoumarin impurities. For example, the compositions may comprise less than 500 ppm furanocoumarin impurities. The composition may comprise from about 0.0001% to about 100% bakuchiol. For example, in certain embodiments the composition comprises from about 0.1% to about 2% bakuchiol or from about 0.5% to about 1% bakuchiol. In other examples the composition comprises about 0.5% or about 1.0% bakuchiol. In certain embodiments, the mammal is a human, and in other embodiments the mammal is in need of prevention, alleviation, reduction or treatment of excess pigmentation resulting from a condition derived from an inflammatory skin disorder, for example the mammal may be in need of treatment for PIH.

The present disclosure demonstrates unexpectedly unique biological properties of synthetic or natural bakuchiol compositions. As shown in Example 5 and Table 4, a Bakutrol composition comprising about 57.35% bakuchiol has unexpectedly high anti-oxidation capacity, especially against super oxide anion (>69,000 μmole TE/g) with a total ORAC value against five predominant reactive species at >92,000 μmole TE/g.

Superoxide is an anion with the chemical formula $O_2^-$. A chronic inflammatory condition, such as acne vulgaris, can have dramatically increased superoxide anion production from keratinocytes, which are stimulated by a gram-positive anaerobic bacterium such as *P. acnes* (Grange P A., et al. Plos Pathogens 2009, 5(7) 1-14). Superoxide is biologically quite toxic and is deployed by the immune system to kill invading microorganisms. In phagocytes, superoxide is produced in large quantities by the enzyme NADPH oxidase for use in oxygen-dependent killing mechanisms of invading pathogens. Superoxide anion and other reactive oxygen species in the inflamed skin can also induce melanogenesis, melanocyte proliferation and melanocyte apotosis, which is a major causative factor of post inflammatory hyperpigmentation. Accordingly, one embodiment of the present disclosure is a method for alleviating, reducing or treating excess pigmentation resulting from a condition derived from an inflammatory skin disorder by reducing superoxide with a composition comprising bakuchiol essentially free of furanocoumarin impurities. In one embodiment, the condition is PIH. In another embodiment, the present disclosure provides a method of reducing melanogenesis or melanocyte proliferation or inhibiting melanocyte apotosis, for example, by reducing superoxide anion. The method comprises administering an effective amount of a composition comprising bakuchiol essentially free of furanocoumarin impurities to a mammal. In certain embodiments, the mammal is a human, and in other embodiments the mammal is in need of reducing melanogenesis or melanocyte proliferation or inhibiting melanocyte apotosis.

As demonstrated in Example 6 and FIG. 3, a composition comprising 77.02% bakuchiol, which is substantially free of impurities, particularly furanocoumarin impurities showed protective effect on oxidative stress induced by 4-teriay-butylphenol (4-TBP). The cytotoxicity to melanocytes from the reactive oxygen species generated by 4-TBP was protected by the bakuchiol compositions at the two concentrations tested. While not wishing to be bound by the theory, the present Applicants believe the unexpected clinical benefits from a synthetic or natural bakuchiol composition of reducing, alleviating, preventing or treating post inflammatory hyperpigmentation (PIH) is derived from its unique and unexpected capacity to neutralize reactive oxygen species, especially superoxide anion, and protect melanocytes from oxidative stress under inflammation conditions that lead to reduced epidermal melanosis and/or dermal melanosis.

In addition to its unexpectedly high anti-oxidation capacity, the present Applicants have discovered that the disclosed bakuchiol compositions are not tyrosinase inhibitors. This is in contrast to other reports which disclose bakuchiol as a skin whitening agent via tyrosinase inhibition (Japanese Patent No. P1107123). This unexpected discovery led the present Applicants to the currently disclosed methods for treating PIH where the pigmentation occurs in a deep skin layer and tyrosinase inhibitors are ineffective. The lack of tyrosinase inhibition of the disclosed bakuchiol compositions is shown in Example 7 and FIG. 4. Both pure Bakuchiol (100%) and enriched Bakuchiol (77.02%) with not more than 100 ppm furanocoumarins from natural sources have no tyrosinase inhibition function at eight different dosages.

Compositions comprising bakuchiol at concentrations of 86.54% and 77.02% bakuchiol, were evaluated for their safety profiles. As shown in Example 9 and Table 6, based on in vitro and human clinical tests, the Bakutrol (UP256) compositions showed no eye irritation, no skin irritation on the normal or scarified skin, no skin contact sensitization, no phototoxicity and no mutagenic toxicity. The topical creams of the Bakuchiol composition were well tolerated in all human and in vitro tests.

As demonstrated in Example 10, a natural bakuchiol composition (Bakutrol™) comprising 77.02% bakuchiol and less than 100 ppm furanocoumarin extracted and enriched from the seeds of *Psoralea corylifolia* was tested in a human clinical trial on subjects with post inflammatory hyperpigmentation (PIH) derived from mild or moderate acne vulgaris. The bakuchiol composition was formulated at 0.5% bakuchiol for topical application. After daily topical application of the 0.5% Bakutrol cream, a dramatic reduction of post inflammatory hyperpigmentation (PIH) was observed in all five subjects. As shown in FIG. 5, all five subjects had at least one grade level reduction of PIH severity. More than 50% improvement of PIH affected facial area was achieved after 8 weeks of continued topical application of the 0.5% Bakutrol cream (FIG. 6). The mean percentage and absolute grade level improvements of both PIH and its severity are summarized in FIGS. 7 & 8. Improvements of more than 40%, or more than one grade level reduction of both PIH and severity, were achieved as early as 4 weeks after using the bakuchiol composition. Substantial reduction of PIH on the affected facial skin sites is clearly evident in the photos of two subjects as shown in FIG. 9. Both subjects showed progressive improvement of skin Post-Inflammatory Hyperpigmentation (PIH) associated with mild and moderate acnes after topical application of a Bakutrol cream.

Table 7 (Example 10) summarizes the clinical out puts for using a furanocoumarin free Bakuchiol composition (i.e., Bakutrol) in comparison to popular acne treatment products which contain either an anti-microbial or an anti-inflammatory or combinations thereof. The data in Table 7 clearly demonstrates that the furanocoumarin free Bakuchiol composition not only improved inflammatory and non-inflammatory lesion counts, but also significantly improved skin Post-Inflammatory Hyperpigmentation. The PIH benefit from the Bakuchiol composition is not expected based on its lacks of tyrosinase inhibition activity.

Table 8 (Example 11) presents data showing reduction in PIH grade (i.e., extent of pigmentation). The data clearly shows that bakuchiol is more effective than both placebo and salicylic acid for treatment of PIH. Furthermore, the present applicants have also discovered that bakuchiol (or compositions comprising the same) are effective for treatment of inflammatory lesions, such as acne lesions. Table 9 (Example 11) demonstrates the effectiveness of bakuchiol for treatment of inflammatory lesions compared to treatment with placebo or salicylic acid.

In addition to methods comprising treatment with compositions comprising bakuchiol, the present invention includes embodiments wherein a mammal is treated with a composition comprising bakuchiol and salicylic acid. For example, the present applicants have discovered that salicylic acid is effective for treatment of non-inflammatory lesions, while bakuchiol is effective for treatment of inflammatory lesions. Accordingly, one embodiment of the present invention is directed to a method of treating inflammatory lesions (e.g., acne lesions), the method comprising administering an effective amount of a composition comprising bakuchiol or a pharmaceutically acceptable salt thereof to a mammal. Another embodiment is directed to a method of treating inflammatory and/or non-inflammatory lesions (e.g., acne lesions), the method comprising administering an effective amount of a composition comprising bakuchiol and salicylic acid (or pharmaceutically acceptable salts thereof)

to a mammal. Other embodiments include treatment of non-inflammatory lesions by administering an effective amount of a composition comprising salicylic acid or a pharmaceutically acceptable salt thereof to a mammal. In certain embodiments of the foregoing, the mammal is a human. In other embodiments, the mammal is in need of treatment for inflammatory and/or non-inflammatory lesions, such as acne.

In addition to treatment of lesions, the combination of bakuchiol and salicylic acid is effective for treating any of the foregoing conditions (e.g., PIH, reducing melanogenesis, reducing melanocyte proliferation or preventing melanocyte apotosis, etc.). Accordingly, some embodiments are directed to treatment with a composition comprising bakuchiol and salicylic acid. Other embodiments include a composition comprising bakuchiol or a pharmaceutically acceptable salt thereof, salicylic acid or a pharmaceutically acceptable salt thereof and a pharmaceutically acceptable carrier.

The foregoing methods are effective to substantially eliminate inflammatory and/or non-inflammatory lesions. For example in some embodiments the methods reduce lesions from about 1% to about 99% or from about 10% to about 90%. In other embodiments, the methods reduce lesions by greater than 50%.

The ratio of bakuchiol to salicylic acid is not particularly limited and can be determined by one of ordinary skill in the art based on the desired result. For example, in some embodiments the weight ratio of bakuchiol to salicylic acid ranges from about 1:100 to about 100:1. In other embodiments, the weight ration ranges from about 10:90, about 20:80, about 30:70, about 40:60, about 50:50, about 60:40, about 70:30, about 80:20 to about 10:90. The compositions may be formulated according to any of the formulations described herein.

C. Formulation of Bakuchiol Compositions

The bakuchiol compositions of the present disclosure can be formulated by any means known to those of skill in the art. As shown in Example 8 and Table 5, the compositions of the present disclosure can be formulated as pharmaceutical, cosmetic or dermatological compositions, and can include other components such as a pharmaceutically and/or cosmetically acceptable actives, excipient, adjuvant, carrier or combinations thereof. An excipient is an inert substance used as a diluent or vehicle for dermatological and cosmetically accepted products and drugs. Examples of such excipients include, but are not limited to water, buffers, saline, glycerin, hydrated silica, propylene glycol, aluminum oxide, carrageenan, cellulose gum, titanium dioxide, Ringer's solution, dextrose solution, mannitol, Hank's solution, preservatives and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran.

In Example 8, compositions of the present disclosure were formulated in transcutol, or caprylic triglyceride, or polysorbate-20, or purified water or combinations of two or more of the above vehicle. Excipients can also contain minor amounts of additives, such as EDTA, disodium DDTA, BHA, BHT, diammonium citrate, nordihydroguaiaretic acid, propyl gallate, sodium gluconate, sodium metabisulfite, t-butyl hydroquinone, $SnCl_2$, $H_2O_2$, and 2,4,5-trihydroxybutyrophenone, vitamin C, vitamin E, vitamin E acetate, phenonip, and other substances that enhance isotonicity and chemical stability.

Examples of substances for adjusting the pH of the formulation include sodium hydroxide, sodium carbonate, sodium bicarbonate, pentasodium triphosphate, tetrasodium pyrophosphate, sodium lauryl sulfate, calcium peroxide, phosphate buffer, bicarbonate buffer, tris buffer, histidine, citrate, and glycine, or mixtures thereof. Examples of flavors include, but are not limited to thimerosal m- or o-cresol formalin, fruit extracts and benzyl alcohol. Standard formulations can either be liquid or solids, which can be taken up in a suitable liquid as a suspension or solution for administration. Thus, in a non-liquid formulation, the excipient can comprise dextrose, human serum albumin, preservatives, etc., to which sterile water or saline can be added prior to administration.

In one embodiment, the bakuchiol composition is formulated with other active compounds that target a different mechanism of action for reduction of skin pigmentation. Such actives include but are not limited to, hydroquinone, monobenzylether, arbuting, deoxyarbutin, mequinol, N-acetyl-4-S-cysteaminylphenol, kojic acid, azelaic acid, glycolic acid, gentisic acid, favonoids, aloesin, stilbene and stilbene derivatives, licorice extract, bearberry extract, mulberry extract, aloe vera gel, glabridin, vitamin C derivatives, magnesium ascorbyl phosphate, tetrahexyldecyl ascorbate, vitamin e derivatives, tranexamic acid and its derivatives, biomimetric of TGF-B proteins, centaureidin, niacinamide, PAR-2 inhibitors, lectins, neoglycoproteins, resorcinol and its derivatives, and Nivitol™.

In another embodiment, the composition comprises anti-inflammatory and anti-microbial agents that can synergistically work with the bakuchiol composition to reduce the infection, infection related inflammation, and acceleration of epidermal turnover. Such actives include but are not limited to α-hydroxyacids, salicylic acid, linoleic acid, retinoids, benzoyl peroxide, sodium sulfacetamide, clindamycin, erythromycin, dapsone, tetracycline, doxycyclin, minocyclin, zinc, estrogen and its derivatives, anti-androgens, sulfur, corticosteroids, cortisone, tazarotene, curcumin extract, acacia extract, scutellaria extract, green tea extract, and grape seed extract.

In certain embodiments, the composition comprises an adjuvant or a carrier. Adjuvants are typically substances that generally enhance the biological response of a mammal to a specific bioactive agent. Suitable adjuvants include, but are not limited to, Freund's adjuvant; other bacterial cell wall components; aluminum, calcium, copper, iron, zinc, magnesium, stannous based salts; silica; microdermabrasion agents, polynucleotides; toxoids; serum proteins; viral coat proteins; other bacterial-derived preparations; gamma interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives such as Quil A (available from Superfos Biosector A/S, Denmark). Carriers are typically compounds that increase the half-life of a therapeutic composition in the treated host. Suitable carriers include, but are not limited to, polymeric controlled release formulations, biodegradable implants, liposomes, nano-capsulation, nano-particles, bacteria, viruses, oils, esters, and glycols.

In other examples, the composition is prepared as a controlled release formulation, which slowly releases the composition into the host. As used herein, a controlled release formulation comprises a composition of bakuchiol in a controlled release vehicle. Suitable controlled release vehicles will be known to those skilled in the art. Examples of controlled release formulations are biodegradable (i.e., bioerodible) and include capsules.

In one embodiment, a suitable ointment is comprised of the desired concentration of UP256 (bakuchiol) that is an efficacious, nontoxic quantity generally selected from the range of 0.001% to 100% based on total weight of the topical formulation, from 65% to 100% (for example, 75% to 96%) of white soft paraffin, from 0% to 15% of liquid paraffin, and from 0% to 7% (for example 3 to 7%) of lanolin or a derivative or synthetic equivalent thereof. In another embodiment the ointment may comprise a polyethylene-liquid paraffin matrix.

In one embodiment, a suitable cream is comprised of an emulsifying system together with the desired concentration of UP256 (bakuchiol) synthesized and/or isolated from a single plant or multiple plants as provided above. The emulsifying system is preferably comprised of from 2 to 10% of polyoxyethylene alcohols (e.g., the mixture available under the trademark Cetomacrogol™1000), from 10 to 25% of stearyl alcohol, from 20 to 60% of liquid paraffin, and from 10 to 65% of water, together with one or more preservatives, for example from 0.1 to 1% of N,N"-methylenebis(N'-[3-(hydroxymethyl)-2,5-dioxo-4-imidazolidinyl]urea](available under the name Imidurea USNF), from 0.1 to 1% of alkyl 4-hydroxybenzoates (for example the mixture available from Nipa Laboratories under the trade mark Nipastat), from 0.01 to 0.1% of sodium butyl 4-hydroxybenzoate (available from Nipa Laboratories under the trade mark Nipabutyl sodium), and from 0.1 to 2% of phenoxyethanol.

In one embodiment, a suitable gel is comprised of a semi-solid system in which a liquid phase is constrained within a three dimensional polymeric matrix with a high degree of cross-linking. The liquid phase may be comprised of water, together with the desired amount of UP256 (bakuchiol), from 0.01 to 20% of water-miscible additives, for example glycerol, polyethylene glycol, or propylene glycol, and from 0.01 to 10%, preferably from 0.5 to 2%, of a thickening agent, which may be a natural product, for example tragacanth, pectin, carrageen, agar and alginic acid, or a synthetic or semi-synthetic compound, for example methylcellulose and carboxypolymethylene (carbopol); together with one or more preservatives, for example from 0.1 to 2% of methyl 4-hydroxybenzoate (methyl paraben) or phenoxyethanol-differential. Another suitable formulation, is comprised of the desired amount of UP256 (bakuchiol), together with from 70 to 90% of polyethylene glycol (for example, polyethylene glycol ointment containing 40% of polyethylene glycol 3350 and 60% of polyethylene glycol 400, prepared in accordance with the U.S. National Formulary (USNF)), from 5 to 20% of water, from 0.02 to 0.25% of an anti-oxidant (for example butylated hydroxytoluene), and from 0.005 to 0.1% of a chelating agent (for example ethylenediamine tetraacetic acid (EDTA)).

The term soft paraffin as used above encompasses the cream or ointment bases white soft paraffin and yellow soft paraffin. The term lanolin encompasses native wool fat and purified wool fat. Derivatives of lanolin include in particular lanolins which have been chemically modified in order to alter their physical or chemical properties and synthetic equivalents of lanolin include in particular synthetic or semisynthetic compounds and mixtures which are known and used in the pharmaceutical and cosmetic arts as alternatives to lanolin and may, for example, be referred to as lanolin substitutes.

One suitable synthetic equivalent of lanolin that may be used is the material available under the trademark Softisan™ known as Softisan 649. Softisan 649, available from Dynamit Nobel Aktiengesellschaft, is a glycerine ester of natural vegetable fatty acids, of isostearic acid and of adipic acid; its properties are discussed by H. Hermsdorf in Fette, Seifen, Anstrichmittel, Issue No. 84, No. 3 (1982), pp. 3-6.

The other substances mentioned hereinabove as constituents of suitable ointment or cream bases and their properties are discussed in standard reference works, for example US Pharmacopoeia. Cetomacrogol 1000 has the formula $CH_3(CH_2)_m(OCH_2CH_2)_nOH$, wherein m may be 15 or 17 and n may be 20 to 24. Butylated hydroxytoluene is 2,6-di-tert-butyl-p-cresol. Nipastat is a mixture of methyl, ethyl, propyl and butyl 4-hydroxybenzoates.

The compositions disclosed herein may be produced by conventional pharmaceutical techniques. Thus the aforementioned compositions, for example, may conveniently be prepared by mixing together at an elevated temperature, for example 60-70° C., the soft paraffin, liquid paraffin if present, and lanolin or derivative or synthetic equivalent thereof. The mixture may then be cooled to room temperature, and, after addition of the hydrated crystalline calcium salt of mupirocin, together with the corticosteroid and any other ingredients, stirred to ensure adequate dispersion.

Finally, bakuchiol has a partition coefficient of log P=6.13. The partition coefficient of a chemical compound provides a thermodynamic measure of its hydrophilicity/lipophilicity balance and thus its potential bioavailability. Having a partition coefficient of 6.13 means this compound has high cell membrane penetration and bioavailability when formulated in a delivery system. The skin penetration of the active compound—bakuchiol in a skin care cream was quantified in an ex-vivo test on isolated human skin. The results showed a good skin penetration and bioavailability. In certain embodiments, the disclosed compositions comprise a skin penetration enhancer.

D. Administration of Bakuchiol Compositions

The compositions of the present disclosure can be administered by any method known to one of ordinary skill in the art. For example, the disclosed compositions can be administered internally or topically. The modes of administration include, but are not limited to, enteral (oral) administration, parenteral (intravenous, subcutaneous, and intramuscular) administration and topical application. In certain embodiments, the compositions are administered topically.

The content of a bakuchiol composition in the finished skin care products for PIH can range from 0.001% to 99.9% by weight. In some embodiments, the composition comprises from 0.1% to 2% bakuchiol. In other examples the composition comprises 0.5% or 1.0% bakuchiol. In certain embodiments the amount of bakuchiol composition in a PIH skin care cream ranges from 0.5-1%. The methods according to this disclosure comprise administering internally or topically to a mammal a therapeutically effective amount of a composition comprising bakuchiol, which is totally synthesized or isolated from natural sources (or a combination thereof) and is substantially free of impurities, particularly furanocoumarin impurities (e.g., less than 500 ppm).

The therapeutic agents of the instant disclosure can be administered topically by any suitable means known to those of skill in the art for topically administering therapeutic compositions. Such modes of administration include, but are not limited to, as an ointment, gel, lotion, or cream base or as an emulsion, as a patch, dressing or mask, a nonsticking gauze, a bandage, a swab or a cloth wipe. Such topical application can be locally administered to any affected area, using any standard means known for topical administration.

A therapeutic composition can be administered in a variety of unit dosage forms depending upon the method of administration. For particular modes of delivery, the therapeutic compositions can be formulated in an excipient as discussed above. A therapeutic composition of the present disclosure can be administered to any host, preferably to mammals, and more preferably to humans. The particular mode of administration will depend on the condition to be treated.

Regardless of the manner of administration, the specific dose is calculated according to the approximate body weight of the host. Further refinement of the calculations necessary to determine the appropriate dosage for treatment involving each of the above mentioned formulations is routinely made by those of ordinary skill in the art and is within the scope of tasks routinely performed by them without undue experimentation, especially in light of the dosage information and assays disclosed herein. These dosages may be ascertained through use of the established assays for determining dosages utilized in conjunction with appropriate dose-response data. In certain embodiments, the dose of the composition comprising bakuchiol ranges from 0.001 to 200 mg per kilogram of body weight.

The following examples are provided for purposes of illustration, not limitation.

EXAMPLES

Example 1

Quantification of Bakuchiol, Psoralen and Isopsoralen by HPLC

The amount of bakuchiol, psoralen and isopsoralen in the extracts, fractions, process materials, ingredients and final formulated products were quantified by high pressure liquid chromatography (HPLC) using a PhotoDiode Array detector (HPLC/PDA). The targeted compounds were eluted from a Luna Phenyl-hexyl column (250 mm×4.6 mm) using an acetonitrile (ACN) or methanol & water gradient from 36% to 100% ACN over a period of 12 minutes, followed by 100% ACN for three minutes. The detailed HPLC conditions used are set forth in Table 1. A chromatogram of the HPLC separation is shown in FIG. 1. The targeted compounds were identified and quantified based on retention time and UV peak area using commercially available pure bakuchiol, psoralen and isopsoralen as quantification standards. The retention times for the bakuchiol, psoralen and isopsoralen were 18.19 minutes, 7.33 minutes and 7.95 minutes, respectively.

TABLE 1

HPLC Conditions for quantification of Bakuchiol, Psoralen and Isopsoralen

| | |
|---|---|
| Column | Luna Phenyl-hexyl, 150 × 4.6 mm |
| Gradient | 0-8 min 36% ACN/water |
| | 8-20 min 36% ACN/water to 100% ACN |
| | 20-23 min 100% ACN |
| | 23-28 min 36% ACN/water |
| Flow rate | 1 mL/min |
| Detection | 0-11 min 246 nm (for psoralen and angelicin, 7-8 min) |
| | 11-28 min 260 nm (for bakuchiol, 18-19 min) |
| Temperature | 35° C. |
| Standard concentration | 0.1 mg/mL in MeOH for bakuchiol |
| | 0.025 mg/mL for psoralen and angelicin |
| Extract preparation | 0.2 mg/mL in MeOH |
| Linear range | 0.01 mg/mL to 0.15 mg/mL |

Example 2

General Methods for Extraction of Bakuchiol from *Psoralea* Plants

Method A—To a flask was added solvent (100 mL) and *Psoralea corylifolia* seed powder (10 g), and the mixture was shaken on a wrist shaker at room temperature for one hour. The mixture was then passed through a filter and the filtrate collected. The extraction process was repeated one more time with fresh solvent, the filtrates were combined, the solvent removed on a rotoevaporator and the residue dried under high vacuum.

Method B—To a flask was added solvent (50 mL) and *Psoralea corylifolia* seed powder (10 g), and the mixture was refluxed for 40 min. The solution was then filtered and the extraction process was repeated two more times with fresh solvent. The filtrates were combined, and the solvent was evaporated to obtain a dried extract.

Following the above extraction methods, sample plant material was extracted with the following solvents: dichloromethane (DCM), ethyl acetate (EtOAc), acetone, methanol (MeOH), petroleum ether (BP 35-60° C.) and petroleum ether (BP 60-90° C.). The extracts and plant materials were then analyzed by HPLC analysis as described in Example 1. The results are set forth in Table 2.

TABLE 2

Quantification of Various *Psoralea Corylifolia* Extracts

| | Petroleum Ether (35-60° C.) | DCM | EtOAc | Acetone | MeOH | Petroleum Ether (35-60° C.) | Petroleum Ether (60-90° C.) |
|---|---|---|---|---|---|---|---|
| Extract wt. (g) | 0.5833 | 1.7535 | 1.6710 | 1.8932 | 1.8795 | 0.6457 | 0.9203 |
| % Bakuchiol in Extract | 29.1% | 14.2% | 13.7% | 13.7% | 13.9% | 25.6% | 27.2% |
| % Bakuchiol in Plant | 1.7% | 2.5% | 2.3% | 2.6% | 2.6% | 2.6% | 2.7% |
| Method | Wrist shaker (100 ml/10 g solid) | | | | | Reflux (50 ml/10 g solid) | |

Example 3

Chromatographic Methods for Purifying Bakuchiol Extracts

Various chromatographic methods were utilized for purifying bakuchiol from the crude solvent extract isolated from the seeds of *Psoralea corylifolia* using the method described in Example 2. The efficiency of a specific column enrichment method was demonstrated as a means of obtaining high purity bakuchiol free of contamination by furanocoumarins, particularly psoralen/isopsoralen contamination. Briefly, each empty column cartridge (1.3 cm internal diameter (ID) and 20 mL capacity, from Bio-Rad) was packed with a different media and eluted with different solvents in an attempt to separate the furanocoumarin impurities from bakuchiol. The fractions (10 mL per fraction) were collected in test tubes and analyzed with silica gel TLC plates developed with 20% EtOAc/petroleum ether. The targeted compounds, bakuchiol, psoralen and isopsoralen, were identified based on their retention times, which were determined using solutions of standard compounds. The results are set forth in Table 3. Many of the methods described in Table 3 were useful for the separation of furanocoumarins and bakuchiol from both synthetic and natural sources, however the cost of this methodology may not be economically feasible for large scale production.

TABLE 3

Summary of Column Chromatographic Separation of Bakuchiol from Furanocoumarins in Crude Extracts of Psoralea Corylifolia

| Media | Column size/ Extract Loading | Elution Solvent | Results |
| --- | --- | --- | --- |
| $Al_2O_3$ (neutral) (J. T. Baker) | 2 mL/25 mg | 1. Petroleum ether 2. EtOAc 3. MeOH | Little separation |
| XAD-4 (amerlite polystyrene resin) | 5 mL/19 mg | MeOH/water gradient in 20% increments from 100% water to 100% MeOH | No separation |
| XAD-7 (amerlite polyacrylate resin) | 8 mL/16 mg | Pet. ether/EtOAc gradient in 20% increments from 100% petroleum ether to 100% MeOH | Some separation |
| | | MeOH/water gradient in 20% increments from 100% water to 100% MeOH | Little separation |
| Polyamide | 5 mL/50 mg | 1. Petroleum ether 2. 5% acetone/pet. ether 3. Acetone | No separation |
| LH-20 | 8 mL/50 mg | Petroleum ether | No separation |
| Silica gel | 5 mL/50 mg | 1. Petroleum ether 2. 15% EtOAc/pet. ether | Good separation |
| CG-71md | 5 mL/50 mg | 1. Petroleum ether 2. Acetone | No separation |
| CG-161cd | 5 mL/50 mg 6 mL/50 mg | Petroleum ether MeOH/water step gradient | No separation Good separation Low yield |

Example 4

Hydrolysis of an Extract Isolated from the Seeds of *Psoralea corylifolia*

A hexane extract or a $CO_2$ super-critical fluid extract of seeds of *Psoralea corylifolia*, which contained about 25% bakuchiol, was mixed with a 1M NaOH solution. The solution was heated in a reaction vessel to a temperature at or above 80° C. for at least one hour. A small portion of the solution was taken from the flask periodically and analyzed by HPLC as described in Example 1. The reaction was stopped after HPLC analysis showed that the peaks for psoralen and isopsoralen had completely disappeared. The reaction mixture was then cooled to room temperature and the aqueous phase was removed. After the solution was washed multiple times with saturated a NaCl solution, the organic layer was extracted with ethyl acetate or other organic solvents. The organic solution was filtered, washed, dried and evaporated to yield a brownish red syrup having a bakuchiol content not less than 50% and a combined total of no more than 100 ppm of psoralen and angelicin (isopsoralen).

Example 5

An I-Oxidation Property of Furanocoumarin Free Bakuchiol Composition

A natural bakuchiol composition (Lot # UP256-0906MP) comprising 57.35% bakuchiol and a combined total of less than 100 ppm psoralen and angelicin (isopsoralen) was evaluated for its antioxidant capacity against peroxy radicals, hydroxyl radicals, peroxynitrite, super oxide anion and singlet oxygen at Brunswick laboratories, Norton, Mass. USA. The total oxygen radical absorbance capacity of the bakuchiol composition was measured according to the published methodology (Ou, B. et al., J Agric and Food Chem, 2001, 49 (10): 4619-4626; Prior, R L. et al., J Agric and Food Chem, 2005, 53: 4290-4302). Results are tabulated in Table 4.

TABLE 4

Anti-oxidation Profile of Bakutrol ™ (UP256)

| Test | Result† | Units |
|---|---|---|
| Antioxidation power against peroxyl radicals | 12,848 | µmole TE/gram |
| Antioxidation power against hydroxyl radicals | 6,262 | µmole TE/gram |
| Antioxidation power against peroxynitrite | 289 | µmole TE/gram |
| Antioxidation power against super oxide anion | 69,929 | µmole TE/gram |
| Antioxidation power against singlet oxygen | 3,067 | µmole TE/gram |
| Total ORAC$_{FN}$ (sum of above) | 92,395 | µmole TE/gram |

*The acceptable precision of the ORAC assay is <15% relative standard deviation.
†Liquid samples weighed and extracted due to viscosity.
There are five predominant reactive species found in the body: peroxyl radicals, hydroxyl radicals, peroxynitrite, super oxide anion, and singlet oxygen. Total ORAC$_{FN}$ provides a measure of the total antioxidant power of a food/nutrition product against the five predominant reactive species.

Example 6

Evaluation of a Bakuchiol Composition for Antioxidation Protective Effect on 4-TBP Cytotoxicity A natural bakuchiol composition comprising 77.02% bakuchiol and a combined total of less than 100 ppm psoralen and angelicin (isopsoralen) was tested for its antioxidant property by assessing its ability to prevent 4-tertiarybutyiphenol (4-TBP) induction of oxidative stress during a 5-day treatment period using compound concentrations at the 95% viability dose. Oxidative stress was determined by assaying the generation of Reactive Oxygen Species (ROS) using the Image-iT Live Green Reactive Oxygen Species Detection Kit (InVitrogen). In this assay, carboxy-2',7'-dichlorodihydrofluorescein diacetate is added to cultured cells for 30 minutes where it diffuses into melanocytes and is hydrolyzed by intracellular esters to 2',7'-dichlorofluorescein (DCF) which reacts with ROS to generate fluorescent DCF. After 5 days of treatment with 200 µM or 400 µM of 4-TBP, the generation of ROS in melanocytes demonstrated a dose response (i.e., moderate to robust, respectively), whereas the untreated and DMSO treated melanocytes exhibited no ROS generation. When the treatment protocol included the test compounds, UP256 (bakuchiol) demonstrated strong antioxidant property as shown in FIG. 3.

Example 7

Tyrosinase Inhibition Activity of a Bakuchiol Composition

Two natural bakuchiol compositions comprising 77.02% bakuchiol (100% purity) were tested for tyrosinase inhibition activity. Both materials contained a combined total of less than 100 ppm total psoralen and angelicin (isopsoralen).

A tyrosinase inhibition assay was carried out using the method reported by Jones et al. (2002) Pigment. Cell Res. 15:335. Using this method, the conversion of L-Dopa, a substrate of tyrosinase, into dopachrome was followed by monitoring absorption at 450 nm. Tyrosinase was prepared in 50 mM potassium phosphate buffer, pH 6.8 (assay buffer) at 2000 U/ml and stored at −20° C. in 1 ml aliquots prior to use. For use in assays, stock enzyme solutions were thawed and diluted to 200 U/ml with assay buffer. A 2 mM working solution of substrate, L-DOPA, was prepared in assay buffer for each assay. Samples were dissolved in 10% DMSO (0.5 ml) and diluted to 5 ml with assay buffer. The reaction mixture comprised 0.050 ml 2 mM L-DOPA, 0.050 ml 200 U/ml mushroom tyrosinase and 0.050 ml inhibitor. Reaction volume was adjusted to 200 µl with assay buffer. Assays were performed in 96 well Falcon 3097 flat-bottom microtiter plates (Beckton Dickinson, N.J.). Appearance of dopachrome was measured with a WALLAC 1420 Multilable Counter (Turku, Finland). Average velocity was determined from linear enzyme rate as measured by change in absorbance ($\Delta A_{450}$) at 450 nm per minute. Percent inhibition of tyrosinase by test samples was determined by comparison of absorbance of samples versus control using formula (1):

(Negative control absorption−sample absorption)/
Negative control absorption×100     (1)

As shown in FIG. 4, both bakuchiol compositions showed no tyrosinase inhibition activity, while the positive control (kojic acid) showed dose responsive tyrosinase inhibition with and IC50 value of 63.9 µM.

Example 8

Formulation of a Bakuchiol Composition in Cosmetic Cream, Gel, and Lotion

Two natural bakuchiol compositions comprising 86.54% bakuchiol and 77.02% bakuchiol were formulated in a cosmetic vehicle or complicated skin care cream, gel or lotions as demonstrated below.

| Formulation A | |
|---|---|
| Bakuchiol | 1.0% |
| Vitamin E acetate | 0.1% |
| Phenonip | 0.5% |
| Transcutol | 98.4% |

| Formulation B | |
|---|---|
| Bakuchiol | 1.0% |
| Vitamin E acetate | 0.1% |
| Caprylic triglyceride | 98.4% |
| Phenonip | 0.5% |

| Formulation C | |
|---|---|
| Bakuchiol | 1.0% |
| Polysorbate-20 | 15.0% |
| Transcutol | 5.0% |
| Vitamin E acetate | 0.1% |
| Purified water | 78.2% |
| Phenonip | 0.5% |

TABLE 5

Formulation D

| No. | Material | INCI Name |
|---|---|---|
| 1 | D.I.WATER | Water |
| 2 | Gemseal 40 | C15-19 Alkane |
| 3 | GLYCERIN | Glycerin |
| 4 | 1.3-B.G | Butylene Glycol |
| 5 | Carbopol#940 | Carbomer |
| 6 | ARLATON 2121 | Sorbitan Stearate/Sucrose Cocoate |
| 7 | Salacos 816T | C15-19 Alkane |
| 8 | Sunflower Oil | *Helianthus Annuus* (Sunflower) Seed Oil |

TABLE 5-continued

Formulation D

| No. | Material | INCI Name |
|---|---|---|
| 9 | TREHALOSE | Trehalose |
| 10 | ERITHRITOL | Erythritol |
| 11 | Dow Corning #345 | Cyclomethicone |
| 12 | CALCOL 68 (CETANOL) | Cetanol |
| 13 | STEARIC ACID (EMERSOL#132) | Stearic Acid |
| 14 | CITHROL GMS A/S(AR#165) | Glyceryl Stearate/PEG-100 Stearate |
| 15 | GMS #205 | Glyceryl Stearate SE |
| 16 | BEES WAX | Beeswax |
| 17 | SODIUM HYALURONATE(Hyasol) | Sodium Hyaluronate |
| 18 | Bakuchiol at 0.5% | Hydrolyzed *Psoralea corylifolia* extract |

Example 9

Evaluation of the Safety Profile of a Bakuchiol Composition

Two natural bakuchiol compositions comprising 86.54% bakuchiol and 77.02% bakuchiol and a combined total of less than 100 ppm psoralen and angelicin (isopsoralen) were formulated in a cosmetic vehicle or complicated skin care cream and tested on in vitro models or in human clinical trials for their safety profile. As demonstrated in Table 6, the bakuchiol compositions showed no eye irritation, no skin irritation, no skin allergic contact sensitization and no phototoxicity. The compositions had a solid safety profile at a broad range of concentration levels (20% to 100% by weight of bakuchiol) with good skin penetration properties.

TABLE 6

Results of Bakutrol™ Safety Testing

| TEST NAME | BRIEF DESCRIPTION OF THE TEST PROCEDURE | RESULT |
|---|---|---|
| EPIOCULAR MTT VIABILITY ASSAY | This is a biological assay to evaluate ocular toxicity or irritating potential of a test article by determining the ET50 for MTT viability of EpiOcular samples. | Test Product at the 1% concentration was classified in the minimal to non-irritating category. |
| CHAMBER SCARIFICATION | This is a clinical test to assess the irritating potential of chemical compounds. The test is performed on human subjects whose skin was sensitized by scratching. The variable being tested is the compound's ability to cause irritation of compromised skin. | The effects of 0.5% of the test product on scarified skin were comparable to the saline control at 72 hours. |
| REPEATED INSULT PATCH | This is a clinical test to assess both irritating and allergenic potentials of chemical compounds. The test is performed by repetitive application of the compounds to the skin of healthy volunteers. The variables being tested are the compound's ability to cause erythema or edema. | Under study conditions the test product did not indicate a potential for dermal irritation or allergic contact sensitization. |
| PHOTO-TOXICITY | This is a clinical test to assess phototoxic potential of test compounds. The test is performed on human subjects by application of the compounds to the skin, followed by UV-irradiation, and up to 1 week post-irradiation period. The variables being tested are the compound's ability to cause adverse or unexplained reactions. | The test product was considered non-phototoxic according to reference at the 0.5% concentration tested. |
| AMES | This is a biological assay to assess the mutagenic potential of chemical compounds. The test uses strains of the bacterium that carry specific mutations. The variable being tested is the mutagen's ability to cause a reversion of these mutations. | Test product was not associated with any mutagenic changes at doses up to 3 mg/plate |
| PERCUTANEOUS ABSORBTION | This is an ex-vivo test to assess skin penetration of chemical compounds. The test is performed by single application to cadaver skin. The variable being tested is the percentage of test compound that is absorbed into skin over a certain period of time. | At 0.5% formulation concentration, the data indicates a good penetration profile and absorption into skin over 48 hours. |

Example 10

Clinical Evaluation of a Furanocoumarin-Free Bakuchiol Composition

A natural bakuchiol composition (Bakutrol™) extracted and enriched from the seeds of *Psoralea corylifolia* and comprising 77.02% bakuchiol and less than 100 ppm furanocoumarin was formulated in a cosmetic skin care cream (formulation D, Example 8) and tested in a human clinical trial. The study was a pilot, open label human study to evaluate the clinical benefits of Bakutrol™ at 0.5% concentration after topical application. The study included 5 subjects meeting the exclusion/inclusion criteria for evaluation of the benefits of the natural bakuchiol composition for improvement of Post-Inflammatory Hyperpigmentation (PIH). The duration of the study was 12 weeks. The subjects were instructed to apply the Bakutrol™ 0.5% cream twice a day, morning and night, and return to the site for a total of 9 visits, including the screening visit. The evaluation included Investigator Global Assessment of skin conditions (IGA), and Evaluation of overall grade and severity of skin Post-Inflammatory Hyperpigmentation (PIH) and other associated skin conditions, including Erythema, Dryness, Peeling, Oiliness, Safety, and Tolerability. The subject questionnaires included safety and compliance questions in relation to irritation, skin comfort, use of other products and sunscreens. Photographs were taken at baseline, Week 4, Week 8 and Week 12. Change from baseline in PIH severity, change from baseline in the PIH Grade, and the proportion of success according to the IGA scale were recorded and analyzed. The following 6 levels of PIH grade of severity (0=absent, 1=slight, 2=mild, 3=moderate, 4=moderately severe, 5=severe) and total area of PIH affected facial surface were utilized for the clinical output analyses.

As shown in FIG. 5, all five subjects treated with a topical cream comprising Bakutrol™ at 0.5% had at least one grade reduction of PIH severity. The percentage improvement of PIH affected facial area was more than 50% after 8 weeks of continued application (see FIG. 6). The mean percentage and absolute grade level improvements of both PIH and its severity are summarized in FIGS. 7 & 8. Improvements of more than 40%, or more than one grade level reduction of both PIH and severity, were achieved as early as 4 weeks after using a natural bakuchiol composition extracted and enriched from the seeds of *Psoralea corylifolia* and comprising 77.02% bakuchiol and less than 100 ppm furanocoumarin. Substantial reduction of PIH on the affected facial skin sites is clearly evident in the photos of two subjects as shown in FIG. 9. Both subjects showed progressive improvement of skin Post-Inflammatory Hyperpigmentation (PIH) associated with mild and moderate acnes after topical application of a Bakutrol™ cream.

Table 7 summarizes the clinical outputs for using a furanocoumarin-free Bakuchiol composition compared to popular acne treatment products that contain either an antimicrobial or an anti-inflammatory or a combination thereof. The data clearly demonstrate that the furanocoumarin-free Bakuchiol composition not only improved inflammatory and non-inflammatory lesion counts but also significantly improved skin Post-Inflammatory Hyperpigmentation. The PIH benefit from the Bakuchiol composition is unexpected based on its lack of tyrosinase inhibition as demonstrated in Example 7.

TABLE 7

Clinical Report Summary of Bakutrol and OTC Drugs

| Study 1 10 week study * | | Study 2 12 week study * | | Study 3 12 week Study * | Study 4 12 week Study * |
|---|---|---|---|---|---|
| Benzaclin (5% Benzoyl Peroxide & 1% Clindamycin) N = 120 | Benzoyl peroxide (5%) N = 120 | Clindamycin (1%) N = 120 | Vehicle N = 120 | ClindaGel (1% Clindamycin) N = 162 | Bakutrol (UP256) 0.5% N = 13 |
| Mean percent reduction in inflammatory lesion counts | | | | | |
| 46% | 32% | 16% | +3% | 51% | 33% |
| Mean percent reduction in non-inflammatory lesion counts | | | | | |
| 22% | 22% | 9% | +1% | 25% | 16% |
| Mean percent reduction in total lesion counts | | | | | |
| 36% | 28% | 15% | 0.2% | 38% | 26% |
| Improvement of Post Inflammatory Hyperpigmentation | | | | | |
| 0 | 0 | 0 | 0 | 0 | 62% |

Example 11

Evaluation of a Furanocoumarin-Free Bakuchiol Composition on Diminishing the Effects of Post-Inflammatory Hyperpigmentation The safety and efficacy of a 0.5% (wt/wt) cream of bakuchiol (UP256) was evaluated in a double blind placebo and positive controlled study for the treatment of P1H related to acne. The study evaluated a bakuchiol cream at 0.5% concentration, a 2% Salicylic acid cream and a placebo cream (Vehicle) in an Asian population. The participants were instructed to apply the study creams to the face twice a day (AM/PM). Study participants were given instructions for application and provided with sunscreen.

The study population consisted of male and female subjects older than 18 and younger than 40 years and in generally good health as determined by a medical history. The bakuchiol study arm enrolled 18 subjects, the Salicylic acid (SAL) study arm enrolled 20 subjects, and the placebo study arm enrolled 19 subjects.

The Investigators and study staff discussed and agreed upon a clear definition of PIH as related to acne or other tissue injury (which did not include freckles (Ephilides), solar lentigo (lentigines), or melisma). The PIH grade is a measure of the severity of the hyperpigmentation (higher number=more severe pigmentation). The patient population had a PIH grade >3 and acne was mild to moderate Grade 2-3, the key factor was the PIH as related to current or past inflammatory acne.

Primary Study Objectives:
1. PIH IGA Time Frame: Baseline and weeks 2, 4 and 8
2. PIH % Distribution Time Frame: Baseline and weeks 2, 4 and 8 PIH efficacy was evaluated based on changes from baseline (p<0.05) and over other treatment groups (p<0.05) using t-test or/and ANOVA.

Secondary Objectives: Safety Assessments

Subject's Assessment questionnaires and Tolerability Assessments were collected at Baseline and weeks 2, 4, and 8. Urine pregnancy tests for females of childbearing potential were collected at Baseline and week 8.

Data Analysis
The following data was collected:
1. Change from baseline in PIH Severity;
2. Change from baseline in the PIH Grade; and
3. Change from baseline in the Lesion counts Results:

The data was analyzed from Investigator evaluations at each visit and from photographs taken at the specified time points. The photographs from baseline, week 4, and week 8 were evaluated by a second group of investigators and two independent dermatologists before the study was unblended to further confirm that the population met criteria. The data analyzed is based on confirmed evaluations, there was no photo for week two therefore week two data is not included in the analysis. Table 8 summarizes the data.

TABLE 8

PIH Grade Changes for Study Groups

|  | Baseline | Week 4 | Week 8 | ANOVA (p value) |
|---|---|---|---|---|
| Bakutrol (UP256) | | | | |
| Mean | 3.44 | 2.83 | 2.5 | 0.0083 |
| SD | 0.78 | 0.86 | 0.99 | |
| SEM | 0.18 | 0.2 | 0.23 | |
| N | 18 | 18 | 18 | |
| (t-test) p value | | 0.0005 | 0.0003 | |
| PLACEBO | | | | |
| Mean | 3 | 3.05 | 3 | 0.9712 |
| SD | 0.82 | 0.71 | 0.67 | |
| SEM | 0.19 | 0.16 | 0.15 | |
| N | 19 | 19 | 19 | |
| p value | | 0.5778 | 1 | |
| 2% SAL | | | | |
| Mean | 3.15 | 3.2 | 3.2 | 0.9798 |
| SD | 0.93 | 0.89 | 0.89 | |
| SEM | 0.21 | 0.2 | 0.2 | |
| N | 20 | 20 | 20 | |
| p value | | 0.3299 | 0.3299 | |

The Bakutrol (UP256) group showed significant change in PIH grade (i.e., lower PIH grade) from baseline at week 8 (p<0.05). Additionally, the Bakutrol group showed significant change over placebo at week 8 (p<0.05). The data also show that the bakutrol treated group is the only group that has a time and treatment significant p value (p=0.0083).

TABLE 9

Inflammatory Acne Lesions for All Groups

|  | Baseline | Week 4 | Week 8 | ANOVA OVER TREATMENT TIME |
|---|---|---|---|---|
| Bakutrol (UP256) | | | | |
| Mean | 13.11 | 9 | 5.67 | 0.016 |
| SD | 9 | 6.93 | 4.67 | |
| SEM | 2.12 | 1.63 | 1.1 | |
| N | 18 | 18 | 18 | |
| p value | | 0.0014 | 0.0001 | |
| Salicylic Acid | | | | |
| Mean | 11.2 | 9.25 | 8.65 | 0.513 |
| SD | 6.83 | 8.33 | 6.47 | |
| SEM | 1.53 | 1.86 | 1.45 | |
| N | 20 | 20 | 20 | |
| p value | | 0.0242 | 0.0159 | |
| PLACEBO | | | | |
| Mean | 8.42 | 7 | 5.68 | 0.0985 |
| SD | 4.38 | 3.83 | 3.22 | |
| SEM | 1 | 0.88 | 0.74 | |
| N | 19 | 19 | 19 | |
| p value | | 0.1367 | 0.0021 | |

The Bakutrol (UP256) group showed significant change from baseline at weeks 4 and 8 (p<0.001). The Bakutrol group also showed significant change over placebo at week 8 (p<0.05). In addition UP256 is the only group that reached a greater than 50% decrease of inflammatory lesions at 8 weeks (57%).

There were no significant changes for the Bakutrol (UP256) group in the non-inflammatory lesion category (data not shown); however, the salicylic acid treated groups in the non-inflammatory lesion category reached a p value<0.05 at 4 weeks of treatment.

TABLE 10

Summary of Questionnaire and Investigator Safety Evaluation

| 0.5% Bakutrol UP256 | PLACEBO | 2.0% Salicylic acid | Subject Assessment Category |
|---|---|---|---|
| 1 | 2 | 4 | Itching/Burning |
| 0 | 0 | 2 | Skin Discomfort |

Conclusion:

The results show that the Bakutrol (UP256) cream significantly reduced Post Inflammatory Hyperpigmentation (PIH) related to acne after only 4 weeks of topical application. UP256 also significantly reduced inflammatory acne lesions (<0.05) by 57% after 8 weeks.

Bakutrol (UP256) cream had a good safety profile and was well tolerated by study participants. The cosmetic acceptability of the cream was rated as better than, or as good as, that of their previous topical over-the-counter (OTC) acne therapy.

Example 12

Treatment of Inflammatory and Non-Inflammatory Acne Lesions

A composition comprising both bakuchiol and salicylic acid is prepared. Patients having both inflammatory, non-inflammatory, or both types of acne of lesions are treated with the composition. The composition is effective to treat both inflammatory and non-inflammatory lesions with a p value<0.05 at 4 weeks of treatment. The reduction in lesions ranges from about 10% to about 90%.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for preventing, alleviating, reducing or treating excess pigmentation in a deep layer of skin resulting from a condition derived from an inflammatory skin disorder, the method comprising administering to a mammal an effective amount of a composition comprising bakuchiol, or a pharmaceutically acceptable salt thereof, and a pharmaceutically acceptable carrier and less than 500 ppm total furanocoumarin impurities.

2. The method of claim 1, wherein the composition comprises less than 100 ppm total furanocoumarin impurities.

3. The method of claim 1, wherein the composition shows no tyrosinase inhibition activity relative to a kojic acid control.

4. The method of claim 1, wherein the furanocoumarin impurities comprise psoralen, isopsoralen or combinations thereof.

5. The method of claim 1, wherein the inflammatory skin disorder comprises atopic dermatitis, allergic contact dermatitis, incontinent pigmenti, lichen planus, lupus erythematosus, morphea, mechanical trauma, ionizing or nonionizing radiation, burns, laser or drug therapies, skin infection, or combinations thereof.

6. The method of claim 1, wherein the composition comprises 0.001% to 99.9% by total weight of bakuchiol and a pharmaceutically, dermatologically or cosmetically acceptable carrier.

7. The method of claim 1, wherein the composition is administered topically, by aerosol, by suppository, intradermically, intramuscularly or intravenously.

8. The method of claim 1, wherein the composition is formulated for topical administration.

9. The method of claim 1, wherein the composition comprises from about 0.1% to about 2.0% by total weight of bakuchiol.

10. The method of claim 1, wherein the composition comprises about 0.5% by total weight of bakuchiol.

11. The method of claim 1, wherein the method alleviates excess pigmentation.

12. The method of claim 1, wherein the method reduces excess pigmentation.

13. The method of claim 1, wherein the method treats excess pigmentation.

14. The method of claim 1, wherein the excess pigmentation occurs in a papillary dermis layer of skin.

15. The method of claim 1, further comprising reducing super oxide anion.

16. The method of claim 1, further comprising reducing melanogenesis.

17. The method of claim 1, further comprising reducing melanocyte proliferation.

18. The method of claim 1, further comprising preventing melanocyte apoptosis.

19. The method of claim 1, wherein the composition further comprises salicylic acid or a pharmaceutically acceptable salt thereof.

* * * * *